(12) United States Patent
Geißer et al.

(10) Patent No.: US 11,552,637 B2
(45) Date of Patent: Jan. 10, 2023

(54) USER INTERFACE AND MEDICAL DEVICE

(71) Applicant: KARL STORZ SE & Co. KG, Tuttlingen (DE)

(72) Inventors: Romana Geißer, Tuttlingen (DE); Achim Sauter, Tuttlingen (DE); Klaus Storz, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 151 days.

(21) Appl. No.: 17/223,510

(22) Filed: Apr. 6, 2021

(65) Prior Publication Data

US 2021/0320658 A1 Oct. 14, 2021

(30) Foreign Application Priority Data

Apr. 9, 2020 (DE) ...................... 10 2020 110 056.6

(51) Int. Cl.
*H03K 17/96* (2006.01)
*A61B 34/00* (2016.01)

(52) U.S. Cl.
CPC .......... *H03K 17/9625* (2013.01); *A61B 34/25* (2016.02); *H03K 2217/96015* (2013.01)

(58) Field of Classification Search
CPC ................................................. H03K 17/9625
USPC ....................................................... 200/237
See application file for complete search history.

(56) References Cited

U.S. PATENT DOCUMENTS

| | | | |
|---|---|---|---|
| 9,298,324 B1 | 3/2016 | Rowe et al. | |
| 2013/0076206 A1 | 3/2013 | Rosenberg et al. | |
| 2019/0369730 A1 | 12/2019 | Marchant | |
| 2020/0042040 A1 | 2/2020 | Browning et al. | |
| 2020/0057467 A1* | 2/2020 | Kim ..................... | G06F 1/203 |
| 2022/0180710 A1 | 12/2022 | Roberts | |

FOREIGN PATENT DOCUMENTS

| | | |
|---|---|---|
| DE | 10 2004 048 463 A1 | 5/2005 |
| DE | 10 2011 089400 A1 | 6/2013 |
| DE | 10 2019 110 399 A1 | 10/2020 |

OTHER PUBLICATIONS

Office Action, DE102020110056.6, dated Mar. 1, 2021 (in German) (6 pp.).
Search Report, EP 21167310.8 dated Jul. 30, 2021 (7 pp.). (in German).

* cited by examiner

*Primary Examiner* — Tomi Skibinski
(74) *Attorney, Agent, or Firm* — Eversheds Sutherland (US) LLP

(57) ABSTRACT

The present application relates to an operating appliance for interacting with a user, including a transparent cover device, a support device with a sensor cutout, and a pressure switch, wherein the transparent cover device forms an operating area and a lower side lying opposite to the operating area and the support device is arranged on or at the lower side and the pressure switch is located and aligned within the sensor cutout in such a way that a user input by means of a finger of the user on the operating area is detectable by the pressure switch, wherein a finger indentation is provided on the operating area and arranged above the pressure switch.

11 Claims, 1 Drawing Sheet

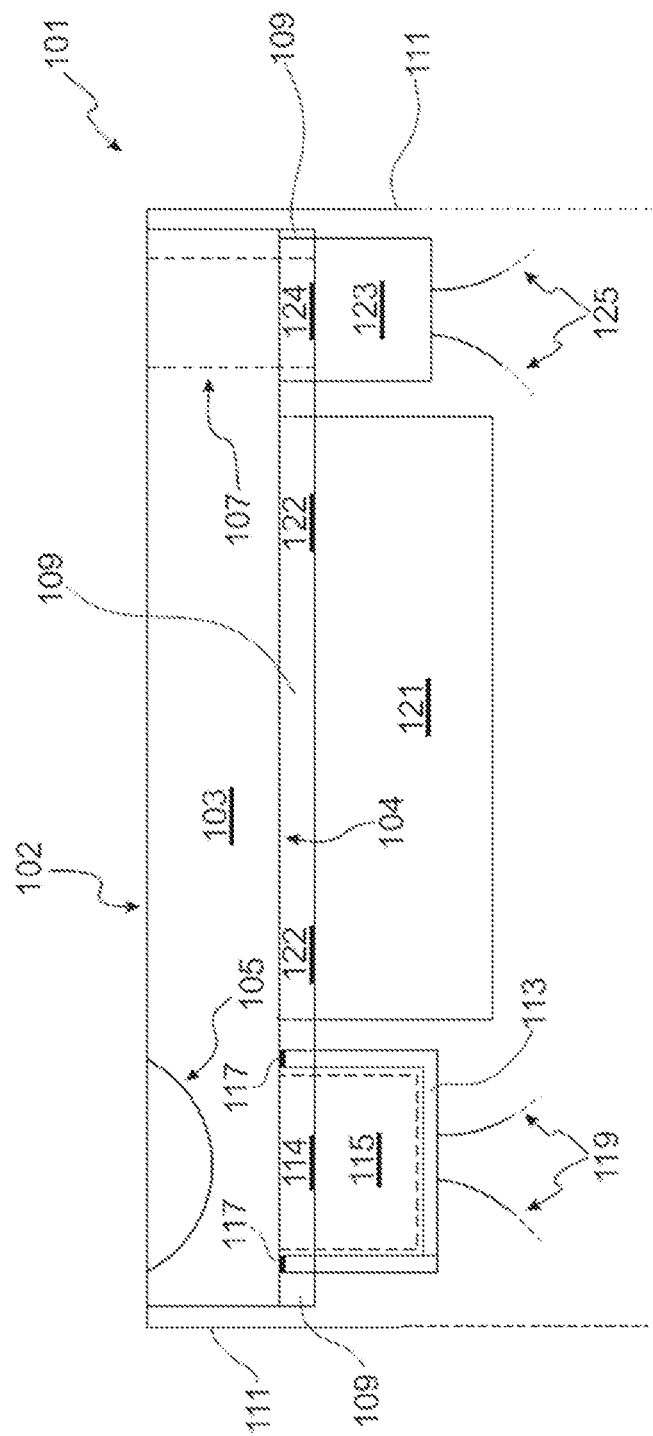

USER INTERFACE AND MEDICAL DEVICE

TECHNICAL FIELD

The invention relates to an operating appliance for interacting with a user, comprising a transparent cover device, a support device with a sensor cutout, and a pressure switch, wherein the transparent cover device forms an operating area and a lower side lying opposite to the operating area and the support device is arranged on or at the lower side and the pressure switch is located and aligned within the sensor cutout in such a way that a user input by means of a finger of the user on the operating area is detectable by the pressure switch, and to a medical apparatus.

BACKGROUND OF THE INVENTION

To be able to better clean operating surfaces of medical apparatuses, such as light sources, insufflators, or pumps, it is desirable for operating elements to be located behind a glass panel. This means that, e.g., a touch-sensitive screen for display and input purposes and, possibly, a further screen and an on/off switch should be arranged behind a glass panel. By way of example, the on/off switch of the apparatus can be embodied as a piezo switch in this case.

The space on the operating surface can be restricted, especially in the case of compact apparatuses. In this case, the switch can be located quite tightly next to the touch-sensitive screen and the adjacent touch-sensitive screen might (also) be operated when the switch is actuated.

By way of example, DE 10 2004 048 463 A1 has disclosed an operating field for a glass cooktop, in which a plurality of proximity sensors are arranged below a glass panel. Furthermore, the operating field has switching mechanisms to counter an operating error.

US 2020/0057467 A1 describes a cellular telephone, in which a biometric sensor is arranged behind the cover glass on the front side of the cellular telephone.

SUMMARY OF THE INVENTION

It is an object of the invention to improve the prior art.

This object is achieved by an operating appliance for interacting with a user, comprising a transparent cover device, a support device with a sensor cutout, and a pressure switch, wherein the transparent cover device forms an operating area and a lower side lying opposite to the operating area and the support device is arranged on or at the lower side and the pressure switch is located and aligned at the sensor cutout in such a way that a user input by means of a finger of the user on the operating area is detectable by the pressure switch, wherein a finger indentation is provided on the operating area and arranged above the pressure switch in such a way that pressing the finger indentation by means of a finger of the user realizes a switching procedure.

As a result, a pressure sensor arranged below a glass surface can be switched in a defined fashion, especially in the case of tight spatial conditions. This furthermore has a consequence that a touch-sensitive screen, for example a touchscreen, which is arranged in the direct vicinity of the pressure switch, is not inadvertently operated since the finger indentation accordingly guides the finger of a user and aligns said finger in a defined fashion with respect to the pressure switch.

Consequently, a pressure switch can advantageously be arranged closer to a touchscreen or, correspondingly, a touchscreen can have a slightly larger configuration.

The following concepts shall be explained:

An "operating appliance" is, e.g., an operator terminal or any other input means, by means of which an operator can control and operate individual control elements, such as a pressure switch or a touchscreen, for example. Consequently, the operating appliance serves to input and/or output data. The operating appliance can be part of an electronic apparatus, for example a medical apparatus, and can facilitate an operation of the apparatus by a user.

An "interaction" should be understood in particular to mean any exchange of data and/or information which involves contact. This can also comprise switching a switch. Additionally, this also comprises the display of information to an operator or user.

The "transparent cover device" protects the display and switching elements situated below the transparent cover device, in particular, and can generally be cleaned well, for example by means of disinfectants. In this case, the transparent cover device can be manufactured from, e.g., a transparent solid plastic or else a glass. In the case of such a transparent cover, for example a glass, a deformation in the region of a few micrometers is sufficient to actuate the switching element, for example. In particular, the cover device is embodied as a planar structure.

The "support device" can stabilize the transparent cover device by way of a supportive function. Additionally, components such as switches, plugs, or else screens, for example, can be fitted or arranged on or in the transparent cover device and can be held by the support device. In particular, the support device has a "sensor cutout". Firstly, the edge formed by the sensor cutout can prevent or reduce the transfer of force to other points of the transparent cover device and can furthermore receive the pressure switch. The support device can likewise have a planar embodiment or be part of an apparatus housing. In particular, it is arranged at and fastened to the cover device in a manner parallel thereto.

Here, the "pressure switch" (also referred to as "pressure sensor") is a piezo switch in particular, which, in a defined manner, can detect spatial changes of a few micrometers on account of an actuation with a finger. Such an actuation in the region of a few micrometers is possible even for the comparatively slight elastic behavior of the transparent cover. To make the pressure switch more easily identifiable, the pressure switch can have a lighting element which is arranged in such a way that the lighting element is identifiable by a user through the transparent cover device. In particular, the lighting element has a circular shape or, accordingly, a ring-shaped. The lighting element can be configured as an LED. Moreover, the lighting element can be configured as an illuminated ring located around a switching point. It is also possible to use piezo switches with an already integrated luminous ring.

Consequently, the transparent cover device has an "operating area", in which the user can actuate the pressure switch or possibly make a selection on a touchscreen, for example using their finger.

Opposite to the operating area, the transparent cover device has a lower side on which the support device, in particular, is arranged and attached, for example by means of an adhesive. The pressure switch or else screens, sensitive screens, plugs, or the like can be arranged on the lower side.

A "finger indentation" is, in particular, a depression in the operating area of the transparent cover device. In this case, the finger indentation can be configured in such a way that a fingertip of a user can be received.

Consequently, the finger indentation conveys a haptic signal to a user, and so it is also conveyed to a user that they can actuate, in defined fashion, a pressure switch situated therebelow.

Advantageously, the force of a finger actuating the pressure switch is transferred in more defined fashion by way of the finger indentation. Consequently, triggering the pressure switch is ensured. Moreover, since less stabilizing material of the transparent cover device is present at the point of the finger indentation, the pressure sensor or, accordingly, the pressure switch can be addressed using less pressure.

On account of the finger indentation being arranged in the operating area, biunique switching, in particular, can be ensured by virtue of the pressure switch being arranged opposite to the finger indentation on the lower side such that the finger indentation is situated above the pressure switch. Consequently, the finger indentation is also situated above the pressure switch in that case, provided the pressure switch is still actuatable in defined fashion by means of a finger in the finger indentation in the case of the normal handling.

A particularly reliable actuation of the pressure switch is ensured, in particular, if the thickness of the finger indentation is between 30% and 70%, in particular between 40% and 60% or in particular between 45% and 55%, of a thickness of the transparent cover device. By way of example, good results are achieved if the transparent cover device has a thickness of 3-5 mm and the finger indentation has a depth value of 1.5-2.5 mm.

In particular, the "thickness of the transparent cover device" is the minimum distance between opposite points of the transparent cover device away from the finger indentation, i.e., consequently, the distance between operating area and lower side.

The "depth value of the finger indentation" is determined, in particular, at the lowest point as seen from the operating area. Consequently, the depth value should simultaneously be determined at the point which represents a minimum in the thickness of the cover device for the finger indentation.

In a further embodiment, the finger indentation is configured to have the shape of a sphere segment or the shape of an ellipsoid segment. These shapes represent, in particular, a very good receptacle for a fingertip of a user.

A shape is understood to have the "shape of a sphere segment" if it represents a cut part of a sphere in form. This can comprise any desired section and consequently the shape of a sphere segment should also be understood to mean the shape of a hemispherical shell. An analogous statement applies to finger indentations having the shape of an ellipsoid, wherein the cuts can be made parallel or orthogonal to the longitudinal axis of an ellipsoid body.

To be optimally set up for the finger of a user, the finger indentation can have a maximum diameter with a value of between 1 cm and 3 cm.

A maximum diameter is the greatest distance that is determinable between the edges of the finger indentation.

In order to be able to detect particularly sensitive pressures on the finger indentation, the pressure switch is configured as a piezo switch. In this case, a "piezo" is a crystal— and is consequently often also referred to as a piezo crystal—, which produces a voltage when pressure is applied. Consequently, the piezo switch can convert the pressure into a voltage, which is electrically and electronically prepared accordingly and which is used for switching purposes, for example for switching an apparatus on and/or off.

In a further embodiment, the pressure switch has a solid housing.

In particular, this housing is an additional housing which, for example, holds the piezo switch or, accordingly, the pressure switch and surrounds said switch laterally and proximally and stabilizes said switch on the outside.

In the present case, it was surprisingly found that the solid (additional) housing allows the pressure of the fingers on the finger indentation to be determined even better. Consequently, fewer accidental operations of the pressure switch were determined within the scope of tests. This is particularly advantageous, in particular, if the solid housing is connected by an edge of the housing to the lower side of the cover device, in particular by means of an adhesive layer. In particular, the additional housing encompasses the pressure switch laterally, wherein an encapsulation of the pressure switch which is open toward the transparent cover device is also realizable. With its edge, the additional housing particularly advantageously supports the transparent cover device by virtue of said edge being connected to the transparent cover device. By way of example, the additional housing can be manufactured from a metal or a metal alloy or else from a plastic. In particular, the additional housing is connected to the pressure switch and forms a unit with the pressure switch. In particular, an edge thickness has a value of between 0.5 mm and 5.0 mm, but it is also possible to realize relatively large edge thickness values of up to 2 cm. In particular, the additional housing can also be integrated as a housing in the support device, i.e., for example, be milled from a basic material of the support device.

The solid housing can be connected to the lower side of the cover device, in particular by means of an adhesive layer, wherein, in particular, the housing is arranged below the finger indentation.

In order to meet the hygiene standards in the field of medicine and in order to be able to treat the surface of the operating appliance with disinfectants, the transparent cover device is configured as a glass layer or, accordingly, as a glass panel. Despite a relatively rigid behavior, thin, industrially available glass in particular has sufficient elasticity to facilitate the actuation of, e.g., a piezo switch in this case. The same also applies to corresponding transparent covers made of a plastic.

Here, "glass" is an amorphous solid, in particular, which predominantly comprises silicon dioxide.

In a further embodiment, the support device has a screen cutout and/or further screen cutouts and/or a device connection cutout and/or further device connection cutouts. Consequently, a screen or further screens, such as touchscreens, can thus be introduced within the screen cutout or the further screen cutout. However, individual display elements and the like are also understood to be a screen in the present case.

An "apparatus connection cutout" is, in particular, a cutout for a plug, by means of which, e.g., power, data, fluids, gases, and the like can be exchanged. A socket can also be understood to mean a plug, wherein, in general, socket and plug form a plug-in system of corresponding parts. In the case of an apparatus connection cutout or a plurality of apparatus connection cutouts, the transparent cover device can likewise have a cutout such that an accordingly corresponding apparatus connection unit can be introduced on the operating area.

Consequently, the operating device can have a further screen, in particular a touch-sensitive screen, such as, e.g., a touchscreen, or further screens.

According to a further aspect, the object is achieved by a medical apparatus which comprises an above-described operating appliance.

BRIEF DESCRIPTION OF THE DRAWING

The invention will be explained in more detail below on the basis of an exemplary embodiment. In detail:

FIG. 1 shows a very schematic side-section representation of an operator terminal of a medical apparatus.

DETAILED DESCRIPTION

An operator terminal 101 of a medical apparatus comprises a 4 mm thick glass panel 103 with an upper side 102 and a lower side 104, and a terminal housing 111. A support plate 109 manufactured from aluminum and comprising a sensor cutout 114, a screen cutout 122, and a plug cutout 124 is directly connected to the glass panel 103 on the lower side 104 by means of adhesive bonding.

A piezo switch 115, which is arranged in a stabilizing additional housing 113, is attached in the sensor cutout 114 on the lower side 104 by means of an adhesive layer 117 such that the adhesive layer 117 connects the lower side 104 to a ring-shaped edge of the additional housing 113.

The stabilizing additional housing 113 has a pot-shaped configuration and is open toward the lower side 104 and consequently encapsulates the piezo switch 115. In one alternative, the additional housing may also be opened at other points in this case, for example by means of additional apertures or openings. A lateral wall strength of the additional housing 113 has a thickness of 1 mm, wherein greater lateral wall strengths can also be implemented here in alternatives.

Directly above the piezo switch 115, the glass panel 103 has an indent-type, spherical segment-shaped depression 105. In the present case, the indent 105 serves as a finger indent and has a maximum diameter of 1 cm to 3 cm and a depth of 2 mm.

At a lateral distance of 1 mm from the additional housing, a touch-sensitive screen 121 has been introduced into the screen cutout 122. This touch-sensitive screen 121 is connected to the support plate 109 and contacts the lower side 104 of the glass panel 103 with its surface.

Laterally next to the touch-sensitive screen 121, a plug housing 123 is arranged in the plug cutout 124 on the lower side 104 of the glass panel 103 and therebelow. Additionally, the glass panel 103 has a circular plug cutout 107.

The operation of the operator terminal is discussed below.

By means of the operator terminal 101, a user switches a medical apparatus on by virtue of placing their finger into the finger indentation 105 and exerting a pressure in the direction of the piezo switch 115. This pressure is detected by the piezo switch 115 and transmitted via associated piezo connectors 119 to an electronics unit (not illustrated), which subsequently activates the touch-sensitive screen 121.

Additionally, the operator links the operator terminal to a medical instrument (not illustrated) by means of a plug, which is introduced into the corresponding plug housing 123 via the upper side 102 of the glass panel 103 and through the plug cutout 107. The corresponding signals are transmitted to the electronics unit via the plug connectors 125.

Subsequently, there is operator guidance by means of the touch-sensitive screen, wherein menu items are selected and approached above the touch-sensitive screen 121 by touching the upper side 102 of the glass panel 103.

This is followed by the treatment of a patient.

After the treatment has been completed, the operator terminal 101 is switched off by virtue of the operator introducing their fingertip into the finger indent 105 and exerting a pressure in the direction of the lower side 104 of the glass panel 103. This pressure is detected by the piezo switch 115 and transmitted to the electronics unit via the piezo connectors 119, whereupon the touch-sensitive screen 121 is switched off.

Finally, the upper side 102 of the glass panel 103 is treated using a disinfectant such that the upper side 102 of the glass panel is sterile.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS

101 Operator terminal of a medical apparatus
102 Upper side of the glass panel
103 Glass panel
104 Lower side of the glass panel
105 Finger indentation
107 Plug cutout
109 Support plate
111 Terminal housing
113 Additional housing
114 Sensor cutout
115 Piezo switch
117 Adhesive layer
119 Piezo connectors
121 Touch-sensitive screen
122 Screen cutout
123 Plug housing
124 Plug cutout
125 Plug connectors

We claim:

1. An operating appliance for interacting with a user, comprising a transparent cover device, a support device with a sensor cutout, and a pressure switch, wherein the transparent cover device forms an operating area and a lower side lying opposite to the operating area and the support device is arranged on or at the lower side and the pressure switch is located and aligned within the sensor cutout in such a way that a user input by means of a finger of the user on the operating area is detectable by the pressure switch, characterized in that a finger indentation is provided on the operating area and arranged above the pressure switch in such a way that pressing the finger indentation by means of a finger of the user realizes a switching procedure.

2. The operating appliance according to claim 1, characterized in that a depth value of the finger indentation is between 30% and 70%, in particular between 40% and 60% or in particular between 45% and 55%, of a thickness of the transparent cover device.

3. The operating appliance according to either of claim 1, characterized in that the finger indentation has the shape of a spherical segment or the shape of an ellipsoid segment.

4. The operating appliance according to claim 1, characterized in that a maximum diameter of the finger indentation has a value of between 1.0 cm and 3.0 cm, for example 2.0 cm.

5. The operating appliance according to claim 1, characterized in that the pressure switch is a piezo switch.

6. The operating appliance according to claim 1, characterized in that the pressure switch has a solid housing.

7. The operating appliance according to claim 6, characterized in that the solid housing is connected to the lower side of the cover device, in particular by means of an adhesive layer and/or by means of a mechanical connection, for example a latching connection, wherein, in particular, the housing is arranged below the finger indentation.

8. The operating appliance according to claim 1, characterized in that the transparent cover device is a glass layer.

9. The operating appliance according to claim 1, characterized in that the support device has a screen cutout and/or further screen cutouts and/or an apparatus connection cutout and/or further apparatus connection cutouts.

10. The operating appliance according to claim 1, characterized in that the operating appliance comprises a further screen, in particular a touch-sensitive screen, or further screens.

11. A medical apparatus, comprising an operating appliance according to claim 1.

* * * * *